(12) United States Patent
Stearns et al.

(10) Patent No.: US 9,427,206 B2
(45) Date of Patent: *Aug. 30, 2016

(54) METHOD AND APPARATUS FOR GATE SPECIFIC MR-BASED ATTENUATION CORRECTION OF TIMED-GATED PET STUDIES

(71) Applicant: General Electric Company, Schenectady, NY (US)

(72) Inventors: Charles William Stearns, Milwaukee, WI (US); Scott David Wollenweber, Waukesha, WI (US); David M. Goldhaber, Shorewood, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/878,077

(22) Filed: Oct. 8, 2015

(65) Prior Publication Data
US 2016/0029990 A1 Feb. 4, 2016

Related U.S. Application Data

(63) Continuation of application No. 14/138,311, filed on Dec. 23, 2013, now Pat. No. 9,168,015.

(51) Int. Cl.
*A61B 6/00* (2006.01)
*G06T 5/50* (2006.01)
(Continued)

(52) U.S. Cl.
CPC ........... *A61B 6/5282* (2013.01); *A61B 5/0033* (2013.01); *A61B 5/0522* (2013.01); *A61B 5/085* (2013.01); *A61B 6/03* (2013.01);
(Continued)

(58) Field of Classification Search
CPC .............. G06T 5/50; G06T 7/0026; G06T 2207/20048; G06T 2207/10088; G06T 2207/10104; G06T 2207/20172; G06T 2207/30004; G06T 2207/30061; G06T 2211/40; G06T 1/1611; G06T 1/2985; A61B 5/0033; A61B 5/0035; A61B 5/0073; A61B 5/0522; A61B 5/055; A61B 5/085; A61B 6/025; A61B 6/03; A61B 6/06; A61B 2019/5236; A61B 6/5258; A61B 6/5264; A61B 8/13; A61B 2019/524
See application file for complete search history.

(56) References Cited

U.S. PATENT DOCUMENTS 5,251,128 A * 10/1993 Crawford ............... A61B 5/113
600/425
6,377,833 B1 * 4/2002 Albert .................. A61B 5/0484
250/363.01
(Continued)

OTHER PUBLICATIONS

Buerger et al., Investigation of MR-Based Attenuation Correction and Motion Compensation for Hybrid PET/MR, IEEE Transactions on Nuclear Science, vol. 59, No. 5, Oct. 2012, 10 pages.*
(Continued)

*Primary Examiner* — Manav Seth
(74) *Attorney, Agent, or Firm* — Grogan, Tuccillio & Vanderleeden, LLP (57) ABSTRACT

A method for producing an attenuation-corrected time-gated PET image comprising includes obtaining a baseline MR image and a cine MR image of a structure; registering the baseline MR image to the cine MR image to create an image transform; and generating a corresponding cine ACF matrix using the image transform, and time-correlating the ACF matrix to a time-gated PET data set to produce an attenuation-corrected time-gated PET image.

20 Claims, 3 Drawing Sheets

(51) Int. Cl.
*G06T 7/00* (2006.01)
*A61B 5/00* (2006.01)
*A61B 5/05* (2006.01)
*A61B 5/085* (2006.01)
*A61B 6/03* (2006.01)
*G01R 33/48* (2006.01)
*G01T 1/161* (2006.01)
*G01T 1/29* (2006.01)

(52) U.S. Cl.
CPC ............ *A61B 6/037* (2013.01); *A61B 6/5247* (2013.01); *A61B 6/5264* (2013.01); *A61B 6/541* (2013.01); *G01R 33/481* (2013.01); *G06T 5/50* (2013.01); *G06T 7/0026* (2013.01); *G01T 1/1611* (2013.01); *G01T 1/2985* (2013.01); *G06T 2207/10084* (2013.01); *G06T 2207/10088* (2013.01); *G06T 2207/10104* (2013.01); *G06T 2207/20048* (2013.01); *G06T 2207/20172* (2013.01); *G06T 2207/30004* (2013.01)

(56) References Cited

U.S. PATENT DOCUMENTS

| | | | | |
|---|---|---|---|---|
| 6,990,368 | B2* | 1/2006 | Simon | A61B 6/481 378/21 |
| 7,117,026 | B2* | 10/2006 | Shao | G06T 7/0038 600/407 |
| 7,180,074 | B1* | 2/2007 | Crosetto | G01T 1/1611 250/370.09 |
| 7,787,675 | B2* | 8/2010 | Pan | G06T 5/50 378/4 |
| 8,098,916 | B2* | 1/2012 | Thielemans | A61B 6/032 382/131 |
| 8,108,024 | B2* | 1/2012 | Carlsen | G06T 7/0024 382/128 |
| 8,208,709 | B2* | 6/2012 | Ding | G06T 5/002 382/131 |
| 8,218,848 | B2* | 7/2012 | Lenglet | G06K 9/342 382/131 |
| 8,535,061 | B2* | 9/2013 | Boutchko | A61B 5/416 434/262 |
| 8,600,132 | B2* | 12/2013 | Razifar | A61B 6/032 382/128 |
| 8,768,432 | B2* | 7/2014 | Ladebeck | A61B 5/055 324/309 |
| 8,866,087 | B2* | 10/2014 | Pistorius | G01T 1/29 250/363.04 |
| 8,942,445 | B2* | 1/2015 | Foo | G06T 7/0081 382/128 |
| 9,168,015 | B2* | 10/2015 | Stearns | G06T 5/50 |
| 2003/0233039 | A1* | 12/2003 | Shao | G06T 7/0038 600/407 |
| 2006/0237652 | A1* | 10/2006 | Kimchy | A61B 1/05 250/363.02 |
| 2009/0110256 | A1* | 4/2009 | Thielemans | A61B 6/032 382/131 |
| 2010/0204563 | A1* | 8/2010 | Stodilka | G01R 33/481 600/411 |
| 2011/0007958 | A1* | 1/2011 | Salomon | G06T 7/0081 382/131 |
| 2011/0123083 | A1* | 5/2011 | Ojha | G01N 24/08 382/131 |
| 2013/0320973 | A1 | 12/2013 | Fenchel et al. | |

OTHER PUBLICATIONS

Buerger C et al: "Investigaton of MR-Based Attenuation Correction and Motion Compensation for Hybrid PET/MR", IEEE Transactions on Nuclear Science, IEEE Service Center, New York, NY, US, vol. 59, No. 5, Oct. 1, 2012, pp. 1967-1976, XP011474376, ISSN: 0018-9499, DOI: 10.1109/TNS.2012.2209127 p. 1967-p. 1971.

Maes F et al: "Medical image registration using mutual information", Proceedings of the IEEE, IEEE, New York, US, vol. 91, No. 10, Oct. 1, 2003, pp. 1699-1722, XPO11100853, ISSN: 0018-9219, DOI: 10.1109/JPROC.2003-817864 sections II.C and II.D.

Mattes D et al: "PET-CT Image Registration in the Chest Using Free-Form Deformations". IEEE Transactions on Medical Imaging, IEEE Service Center, Piscataway, NJ, US, vol. 22, No. 1, Jan. 1, 2003, pp. 120-128, XP001163888, ISSN: 0278-0062, DOI: 10.1109/TMI.203.809072 equation (16).

Wu T H et al: "Low-dose interpolated average CT for attenuation correction in cardiac PET/CT", Nuclear Instruments & Methods in Physics Research. Section A: Accelerators, Spectrometers, Detectors, and Associated Equipment, Elsevier BV * North-Holland, NL, vol. 619, No. 1-3, Jul. 1, 2010, pp. 361-364, XP027092622, ISSN: 0168-9002 [retrieved on Nov. 10, 2009] the whole document.

Internal Search Report and Written Opinion for International Application No. PCT/US2014/049885, mail date Feb. 6, 2015.

* cited by examiner

$$S(\mu) = -\sum_{l}\sum_{k} p(l,k\backslash\mu)\, log\, \frac{p(l,k\backslash\mu)}{p_T(l\backslash\mu)p_R(k)}$$

METHOD AND APPARATUS FOR GATE SPECIFIC MR-BASED ATTENUATION CORRECTION OF TIMED-GATED PET STUDIES

CROSS-REFERENCE TO RELATED APPLICATIONS

This is a continuation of application Ser. No. 14/138,311 filed Dec. 23, 2013, the priority of which is hereby claimed and the full disclosure of which is hereby incorporated by reference.

BACKGROUND

1. Technical Field

Embodiments of the invention relate generally to enhancing quality of images obtained from PET-MR scanners. Particular embodiments relate to attenuation correction of PET images.

2. Discussion of Art

Positron emission tomography ("PET") machines use one or more rings of scintillators or other detectors to generate electrical signals from gamma rays (photon pairs) that produced from the recombination of electrons, within a target material, and positrons, emitted from decay of a radionuclide packaged in a tracer compound. Typically, recombination events occur within about 1 mm from the radionuclide decay event, and the recombination photons are emitted in generally opposite directions to arrive at different detectors. Paired photon arrivals that occur within a detection window (usually less than a few nanoseconds apart) are counted as indicating a recombination event, and, on this basis, computed tomography algorithms are applied to the scintillator position and detection data in order to locate the various recombination events, thereby producing three-dimensional images of the tracer disposition within the target material.

Typically, the target material is body tissue, the tracer compound is a liquid analogue to a biologic fluid, and the radionuclide is disposed primarily in body tissues that make use of the biologic fluid. For example, a common form of PET makes use of fluorodeoxyglucose ($^{18}$F), which is analogous to glucose with the $^{18}$F radionuclide substituted for one of the hydroxyl groups ordinarily composing glucose. Brain matter, kidneys, and growing cells (e.g., metastasizing cancer cells) preferentially absorb both glucose and fluorodeoxyglucose. Therefore, PET is quite useful in oncologic studies, for localizing particular organs, and for studying metabolic processes.

One challenge in obtaining desired PET image quality is that gamma rays, in the energy spectrum produced by positron-electron interactions, are easily attenuated by typical body tissues and are differently attenuated by different body tissues. Varying attenuation will change the likelihood of detecting the recombination events from the patient, thereby confounding the process of making an image from the PET data. Accordingly, it is highly desirable to provide means for attenuation correction ("AC").

For example, PET often is combined with computed tomography ("CT"), which uses a moving X-ray source and detectors to obtain images of internal structures. X-rays are photons and are attenuated much like the higher-energy photons produced from positron-electron recombination events. However, unlike PET photons, the source strength of CT photons is known. Thus, CT image data is a direct measurement of photon attenuation between source and detectors. Therefore, CT image data provides a useful basis for AC of concurrent PET imaging.

Combined PET-CT scans have proven particularly useful in respiratory-gated studies, for example studies undertaken during normal breathing in order to diagnose or evaluate lung cancer. Respiratory-gated images can reduce motion blurring that would otherwise result from acquisition of the PET image throughout a respiratory cycle. However, accurate reconstruction of respiratory-gated PET studies requires gate-specific attenuation correction information. The simultaneous acquisition of CT and PET data supports gate-specific AC.

For example, consider two elements of a PET detector where the line of response between the detectors passes through the lower thorax of the patient. At peak inspiration that line may pass through the lower lobes of the lung, which will attenuate the 511 keV photons by a relatively small amount. As the patient exhales the liver moves up into the thorax, so that at the end of expiration the same line of response may now pass through soft tissue, which will attenuate the 511 keV photons much more than the lung. If the PET data is gated so that there are different images being acquired at peak-inspiration and end-exhalation, each will benefit from an attenuation correction that corresponds to the actual distribution of attenuating tissue during that phase of the respiratory cycle.

Increasingly, and for a variety of reasons including lifetime radiation dose reduction goals, PET/CT scans are being replaced by combining PET scans with magnetic resonance imaging ("MR"). This new combination ("PET-MR") presents novel technical issues. For example, whereas CT forms an image based on detection of X-rays emitted from a source through a target, MR forms an image based on detection of rotating "relaxation" magnetic fields that are produced within a target by nuclei that have odd atomic numbers, i.e., total number of neutrons and protons not divisible by two, in response to fluctuation of an imposed magnetic field. Thus, MR measures a phenomenon fundamentally different from the photons detected by CT and PET.

One advantage of MR is that magnetic fields do not attenuate in body tissues, so that nucleus location can be determined (using Fourier analysis) based solely on frequency shifting between the imposed magnetic field and the response field. Another advantage is that by careful selection of pulse sequence, distinct tissues or materials can be highlighted. Accordingly, MR frequently is used for differentiating tissue types within a patient, and also is used for identifying fine detail structures. Typically, different pulse sequences are used for tissue differentiation. For example, a T1 pulse sequence can be used to obtain images with water appearing darker and fat brighter. On the other hand, a T2 pulse sequence can be used to obtain an image with fat darker, and water lighter.

Thus, a single apparatus that combines PET and MR (a "PET-MR scanner") can provide fine detail, tissue differentiation, and metabolic data. However, because MR signals do not attenuate in the same way as PET or CT signals attenuate, and because MR signal return is highly dependent on the type of pulse sequence used (with each pulse sequence emphasizing a different material), whereas the PET signal is attenuated by every layer of material intervening between a recombination event and a pair of detectors, single-scan MR image data does not necessarily provide a reliable basis for AC of concurrent PET imaging.

MR imaging has the capability to acquire a volume of images over the respiratory cycle, in a manner known as retrospectively gated cine-MRI. However, the types of MR images that can be acquired in a cine fashion have not been considered suitable for producing PET attenuation correction values. The MR protocols conventionally deemed effective for producing PET attenuation correction values, such as 2-point Dixon water-fat scans, typically require more than 10 seconds to acquire, thus, are not usable for capturing multiple images during a respiratory cycle. Instead, in order to minimize motion blur and other breathing artifacts, these MR image data typically have been acquired during a long breath-hold. However, a breath-held MR image does not show the intermediate lung positions that are needed for accurate AC of a PET scan.

BRIEF DESCRIPTION

Embodiments of the invention provide a method for attenuation correction of a plurality of time-gated PET images of a moving structure. The method includes establishing an ACF matrix, based on a baseline MR image of the structure; developing a plurality of image transforms, each of the image transforms registering the baseline MR image to a respective cine MR image of the moving structure; applying each of the image transforms to the ACF matrix to generate a corresponding cine ACF matrix; time-correlating each of the cine MR images, and its corresponding cine ACF matrix, to one of the plurality of time-gated PET data sets; and producing from each of the time-gated PET data sets an attenuation-corrected time-gated PET image.

Aspects of the invention provide an apparatus for generating a plurality of attenuation corrected time-gated PET images. The apparatus includes a PET-MR scanner; a controller connected in communication with the PET-MR scanner, and an image processor connected in communication with the controller. The controller is configured to acquire a baseline MR image of a structure, acquire a sequence of cine MR images of the structure, and acquire a plurality of time-gated PET data sets of the structure. The image processor is configured to generate a baseline ACF matrix based on the baseline MR image, register the baseline MR image with at least some of the cine MR images, generate cine ACF matrices based on registration of the baseline MR image with the cine MR images, and attenuation correct the time-gated PET data sets based on the cine ACF matrices.

Other aspects of the invention provide a method for attenuation correction of PET imaging. The method includes obtaining, in a first MR acquisition, a baseline MR image suitable for deriving PET attenuation correction factors; and obtaining, in a second MR acquisition, a cine sequence of MR images during a respiratory cycle, concurrent with the respiratory-gated PET study. The method further comprises non-rigidly registering the baseline MR image to each of the cine MR images in order to produce a group of registered MR images that correspond to PET data sets from the respiratory-gated PET study and that are usable for deriving attenuation correction factors. The registered MR images then are used to form attenuation correction factors for their respective time-gated PET data sets.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description. Exemplary embodiments of the present invention are described with respect to combined PET-MR scanners, although embodiments may be adapted for use with other imaging systems.

Aspects of the invention relate to improving the simultaneous collection of PET and MR images by providing attenuation correction (AC) of the PET images based on the MR image data.

Figure 1:
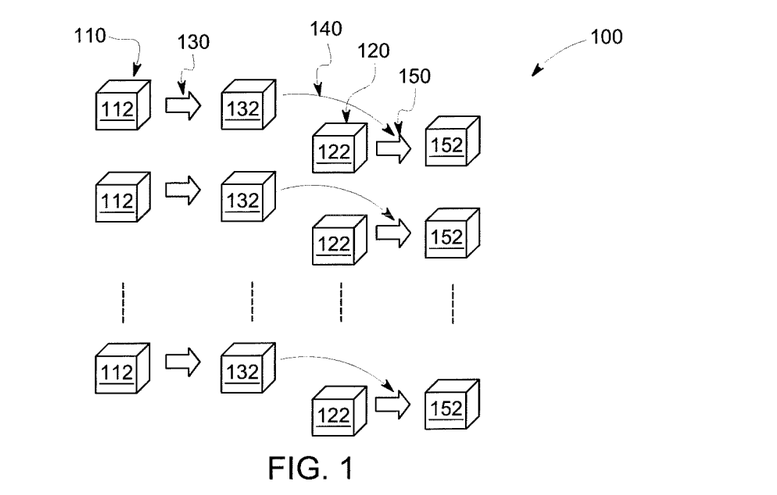
FIG. 1 shows a conventional method for attenuation correction of PET images based on concurrent CT images.

In PET/CT studies, a conventional method 100 of respiratory-gated attenuation (as shown in FIG. 1) includes obtaining 110 a sequence of cine CT images 112 over the same anatomic region and during the same time period as acquiring 120 a sequence of time-gated PET data sets 122. The sequence of cine CT images 112 can be acquired at rates on the order of one image per second, allowing acquisition of six to ten images during a typical respiratory cycle, so that the set of CT images then can be correlated to the gated set of PET raw data files 120. The sequence of CT images 110 are used to derive 130 a sequence of attenuation correction factor matrices ("ACF matrices") 132, and then each ACF matrix is time-correlated 140 to one of the time-gated PET data sets 122 in order to reconstruct 150 a set of attenuation corrected ("AC") PET images 152.

Figure 2:
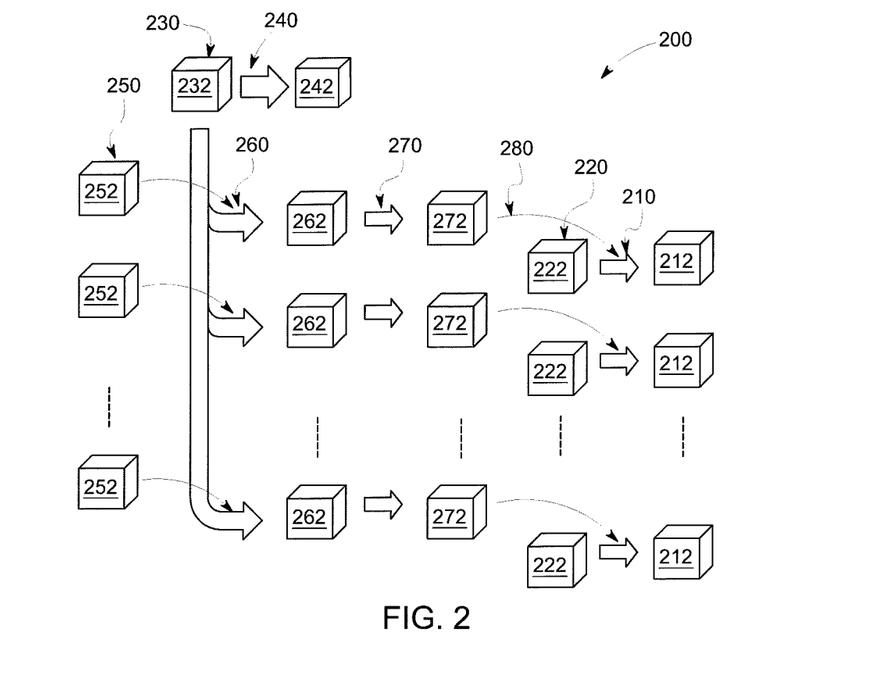
FIG. 2 shows an inventive method for attenuation correction of PET images based on concurrent and baseline MR images, according to a first embodiment of the invention.

FIG. 2 shows a method 200, according to a first embodiment of the invention, for MR-based attenuation correction 210 of a sequence of respiratory-gated PET data sets 222, in order to produce attenuation-corrected PET images 212. In addition to acquiring 220 the PET data sets 222, the method 200 also includes acquiring 230 a tissue-distinguishing or "baseline" MR image 232 that is suitable for later generating 240 a three-dimensional matrix 242 of photon attenuation correction factors ("baseline ACF matrix"). In an embodiment, the baseline MR image 232 is obtained 230 as a substantially static image using a patient breath-hold protocol and a scan protocol suitable for tissue-differentiation study—e.g., a 2-point Dixon scan, which clearly highlights water and fat, and requires in excess often seconds to complete. Although, in certain embodiments, the baseline MR image 232 may be obtained as an averaged image using a tissue-differentiation study during normal respiration, or can be compiled during respiration or during a breath-hold as a composite image from several distinct single-tissue scans, it can be expected that an averaged image or a composite image will not be optimal for subsequently generating the static ACF matrix 242.

Based on the tissues identified in the baseline MR image 232, standard photon attenuation calculations are undertaken for the typical positron-recombination energies in order to generate 240 the baseline ACF matrix 242.

In addition to generating 240 the baseline ACF matrix 242, the method 200 also includes acquiring 250 a sequence of cine MR images 252, and registering 260 each of the cine MR images 252 back to the static MR image 232. In the process of registering 260, a plurality of image transforms 262 are produced, each of the image transforms registering a respective one of the cine MR images 252 with the static MR image 232. In an embodiment, the image transforms are non-rigid. For example, Vemuri, et al., Med. Image Anal. 7:1-20 (2003), describe a "level-sets" algorithm for non-rigid image registration. Other mutual-information-based algorithms (e.g., as taught by Woods (1992) or by Viola and Wells (1994)) can also be used. In most embodiments, the cine MR images 252 are obtained using different (faster) scan protocols than was used for obtaining the baseline MR image 232—e.g., zero-TE or ultra-short-TE scan protocols. Also, in certain embodiments, different scan protocols may be used for different cine MR images 252. Accordingly, registering 260 may also include pixel intensity scaling or shifting to match tissue types between the different scan protocols.

Figure 3:
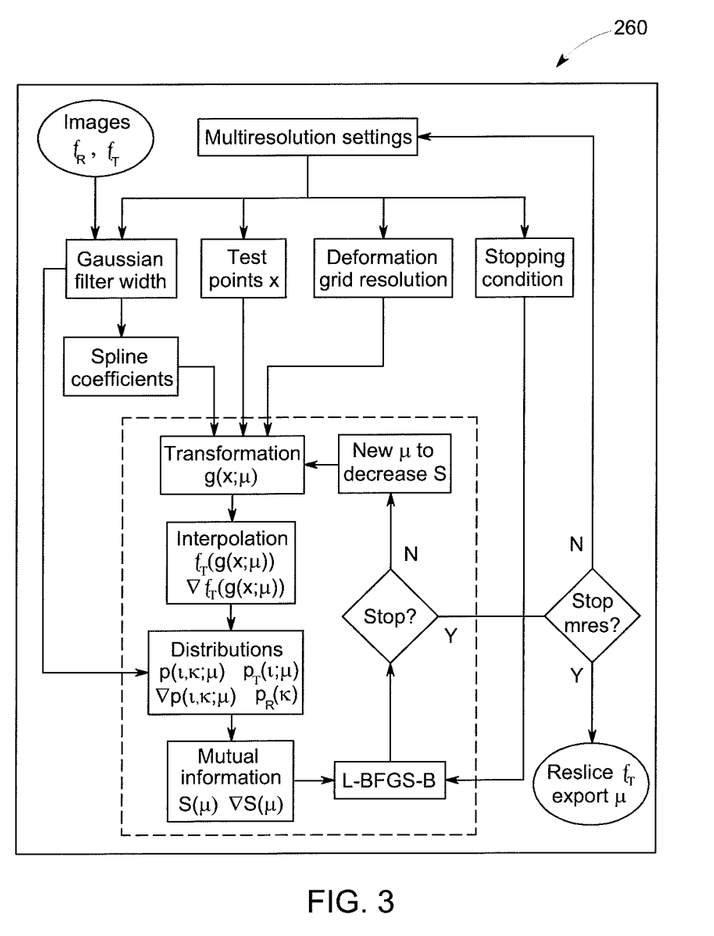
FIG. 3 shows an exemplary process for registering a baseline MR image to a cine MR image, according to an embodiment of the invention.
Figure 4:
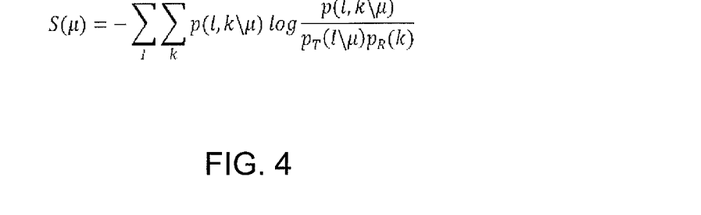
FIG. 4 shows an equation for mutual information of a baseline MR image and a cine MR image.

For example, a locally perturbed (non-rigid) rigid body registration 260, based on mutual information, can proceed as shown in FIG. 3, in which one of the cine images 252 is represented as a differentiable cubic spline function $f_T(x)$, mapping pixel intensities to a linear pixel array, which can be interpolated at any between-pixel position within the set of sampled values composing the image. Similarly, the baseline image 232 is represented as another differentiable cubic spline function $f_R(x)$. A smoothed joint histogram of $$\mu = \arg\min\ S(f_R, f_T \circ g(\cdot|\mu)),$$

which relates the cine image 252 back to the baseline image 232, is defined as a cross product of the two spline functions. The smoothed joint histogram is transformed by applying to the baseline image 232 a set of transformation parameters $\mu = \{\gamma, \theta, \phi, t_x, t_y, t_z; \delta_j\}$, which are chosen to optimize mutual information $S(\mu)$ according to a hierarchical multi-resolution optimization scheme. In the set of transformation parameters $\mu$, $\{\gamma, \theta, \phi\}$ are bulk roll-pitch-yaw Euler angles, $[t_x, t_y, t_z]$ is a bulk translation vector, and $\delta_j$ is a set of deformation coefficients each corresponding to one of a plurality of control points that are defined by a sparse grid that is overlaid on the baseline image 232. Typically, the sparse grid is a regular grid. However, in other embodiments, the sparse grid can be weighted according to pixel intensity or other image metrics. For any given set of non-rigid transformation parameters, mutual information $S(\mu)$ is calculated (as shown in FIG. 4), and mutual information gradients $\nabla S(\mu)$ are calculated, based on probability distributions p, pT, and pR that respectively correspond to: the smoothed joint histogram; a marginal smoothed histogram for the cine image 252; and a marginal smoothed histogram for the baseline image 232. The probability distributions are presumed independent of the transformation parameters. Parameters $\tau$ and $\kappa$, shown in FIG. 4, are pixel intensity histogram bin indexes for the cine image 252 and for the baseline image 232, respectively. Varying the histogram bin sizes can adjust the quality of image registration. The registration is described as locally-perturbed rigid body because it combines local deformation coefficients $\partial j$ with rigid body transforms $\{\gamma, \theta, \phi, [t_x, t_y, t]\}$. Evaluating quality of fit, the registration process 260 either iterates on revised $\mu$, or returns $\mu$ (the image transform 262 that registers the baseline image 232 to the particular cine image 252) for a satisfactory value of $S(\mu)$.

Then, the method 200 includes applying each of the image transforms 262 to the static ACF matrix 242 in order to generate 270 a plurality of cine ACF matrices 272. Each of the cine ACF matrices 272 is time-correlated 280 to one of the plurality of PET data sets 222 within the respiratory-gated PET sequence 220, and is applied 210 to the corresponding PET data set 222 in order to produce a reconstructed and attenuation-corrected PET image 212. In certain embodiments, each of the PET data sets 222 is time-correlated to more than one of the cine ACF matrices, and one of a simple average, a time-weighted average, a velocity-weighted average, or a time-velocity-weighted average is used in applying 210 the plural cine ACF matrices 272 to the PET data set 222.

Although the static MR image acquisition 230 is shown as preceding the cine MR sequence acquisition 250, these steps equally can be accomplished in the other order. In certain embodiments, the cine MR sequence may be duplicated (e.g., before and after the breath-held static image) or the breath-held static image may be duplicated (e.g., before and after the cine sequence). Similarly, registering 260 may be accomplished concurrent with acquiring 250, or after all images have been acquired.

Figure 5:
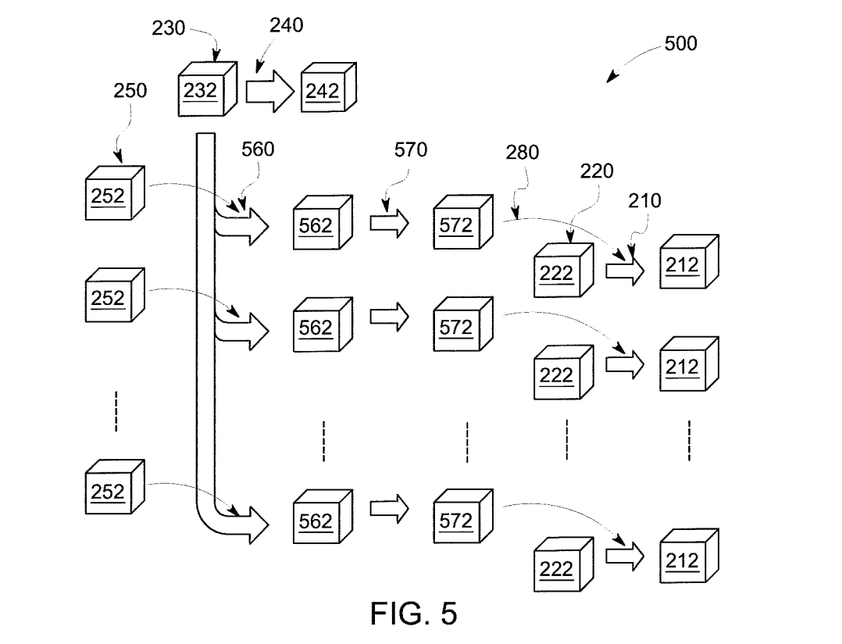
FIG. 5 shows another method for attenuation correction of PET images based on concurrent and baseline MR images, according to a second embodiment of the invention.

Although the plurality of registered ACF matrices 272 are described as being obtained by applying image transforms 262 to the baseline ACF matrix 242, registered ACF matrices 272 also could calculated from the baseline MR image 232, as transformed according to the plurality of image transforms 262. Thus, an alternate method 500 as shown in FIG. 5, according to other embodiments of the invention, includes a first MR acquisition 230 to obtain a static (breath-held) MR image 232 suitable for deriving 240 baseline PET attenuation correction factors 242; and a second MR acquisition 250 to obtain a sequence of cine MR images 252 acquired during a respiratory cycle, concurrent with a respiratory-gated PET study 220. The static MR image 232 is non-rigidly registered to each of the cine MR images 252 in order to produce 560 a group of transformed MR images 562 that correspond to PET data sets 222 from the respiratory-gated PET study and that are usable for deriving 570 attenuation correction factors 572. The registered MR images then are used to form 570 the attenuation correction factors 572, which are time-correlated 280 for producing 210 attenuation-corrected PET images 212 from their respective time-gated PET data sets 222.

Figure 6:
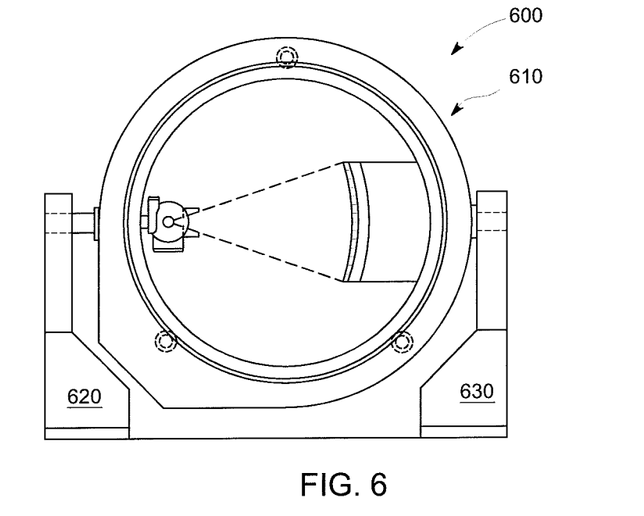
FIG. 6 shows an apparatus for implementing inventive methods for attenuation correction of PET images based on concurrent and baseline MR images, according to embodiments of the invention.

FIG. 6 shows schematically an apparatus 600, according to an embodiment of the invention, for accomplishing the method 200 as described above. The apparatus 600 comprises a combined PET-MR scanner 610, which is connected in communication with a controller 620, the controller in turn connected in communication with an image processor 630. The controller and image processor can both be implemented as separate software in a single computer, or separately in computers co-located with the PET-MR scanner 610; or either or both of the controller 620 and the image processor 630 can be located off-site (remotely) from the PET-MR scanner and/or each other. The controller 620 is configured to accomplish at least acquiring 220 the PET data sets 222, acquiring 230 the baseline MR image 232, and acquiring 250 the sequence of cine MR images 252. The image processor 630 is configured to accomplish at least generating 240 the baseline ACF matrix 242, registering 260 the baseline MR image 232 with each of the sequence of cine MR images 252, generating 270 the plurality of cine ACF matrices 272, and attenuation-correcting 210 the time-gated PET data sets 222 based on the plurality of cine ACF matrices 272. Either the controller 620 or the image processor 630 may be configured to accomplish time-correlating 280 the cine MR images 252 with the time-gated PET data sets 222. Alternatively, the controller 620 and the image processor 630 can be integrated into single software/single processor, or can be implemented in a cloud (SaaS) paradigm.

Thus, embodiments of the invention provide gate-specific attenuation correction factors for time-gated PET data, based on attenuation correction data that is not acquired within the duration of a single gate.

For example, some embodiments of the invention provide a method for attenuation correction of a plurality of time-gated PET images of a moving structure. The method comprises establishing an ACF matrix, based on a baseline MR image of the structure; developing a plurality of image transforms, each of the image transforms registering the baseline MR image to a respective cine MR image of the moving structure; applying each of the image transforms to the ACF matrix to generate a corresponding cine ACF matrix; time-correlating each of the cine MR images, and its corresponding cine ACF matrix, to one of the plurality of time-gated PET data sets; and producing from each of the time-gated PET data sets an attenuation-corrected time-gated PET image. In certain embodiments, the baseline MR image is a composite image. In some other embodiments, the baseline MR image is an averaged image. In some embodiments, the baseline MR image is obtained while the structure is substantially static. In some embodiments, the baseline MR image is obtained using a tissue differentiating scan protocol. In some embodiments, each of the cine MR images uses a same scan protocol as each other of the cine MR images. In certain embodiments, developing the plurality of image transforms comprises pixel intensity scaling or pixel intensity shifting. In certain embodiments, developing the plurality of image transforms comprises iteratively calculating mutual information of a joint pixel intensity histogram constructed from the baseline MR image and from an intermediate transform of the cine MR image. In certain embodiments, developing the plurality of image transforms comprises establishing for each cine MR image an image transform g that comprises rigid transformation parameters $\{\gamma, \theta, \phi, [tx, ty, tz]\}$ and deformation coefficients $\{\delta_j\}$ for registering the baseline MR image to that cine MR image. In certain embodiments, producing an attenuation-corrected time-gated PET image comprises applying to one of the plurality of time-gated PET data sets at least one cine ACF matrix that is time-correlated to that PET data set. In certain embodiments, producing an attenuation-corrected time-gated PET image comprises applying to one of the plurality of time-gated PET data sets one of a simple average, a time-weighted average, a velocity-weighted average, or a time-velocity-weighted average of plural cine ACF matrices that are time-correlated to that PET data set.

Other aspects of the invention provide an apparatus for generating a plurality of attenuation corrected time-gated PET images. The apparatus comprises a PET-MR scanner; a controller connected in communication with the PET-MR scanner, and an image processor connected in communication with the controller. The controller is configured to acquire a baseline MR image of a structure, acquire a sequence of cine MR images of the structure, and acquire a plurality of time-gated PET data sets of the structure. The image processor is configured to generate a baseline ACF matrix based on the baseline MR image, register the baseline MR image with at least some of the cine MR images, generate cine ACF matrices based on registration of the baseline MR image with the cine MR images, and attenuation correct the time-gated PET data sets based on the cine ACF matrices. In certain aspects, the controller is configured to time-correlate each of the cine ACF matrices to one of the time-gated PET data sets. In certain aspects, the image processor is configured to time-correlate each of the cine ACF matrices to one of the time-gated PET data sets. In certain aspects, the image processor is configured to register the baseline MR image to each of the cine MR images using a locally perturbed rigid registration. In certain aspects, the image processor is configured to register the baseline MR image to each of the cine MR images using a mutual information algorithm. In certain aspects, the controller is configured to obtain the baseline MR image while the structure is substantially static. In certain aspects, the controller is configured to concurrently obtain the cine MR images and the PET data sets while the structure is moving. In certain aspects, the image processor is configured to attenuation correct at least one of the plurality of time-gated PET data sets using one of a simple average, a time-weighted average, a velocity-weighted average, or a time-velocity-weighted average of plural cine ACF matrices that are time-correlated to that PET data set.

Other aspects of the invention provide a method for attenuation correction of PET imaging. The method comprises obtaining, in a first MR acquisition, a baseline MR image suitable for deriving PET attenuation correction factors; and obtaining, in a second MR acquisition, a cine sequence of MR images during a respiratory cycle, concurrent with the respiratory-gated PET study. The method further comprises non-rigidly registering the baseline MR image to each of the cine MR images in order to produce a group of registered MR images that correspond to PET data sets from the respiratory-gated PET study and that are usable for deriving attenuation correction factors. The registered MR images then are used to form attenuation correction factors for their respective time-gated PET data sets.

In yet other aspects of the invention, a method for producing an attenuation-corrected time-gated PET image includes obtaining a baseline MR image and a cine MR image of a structure, registering the baseline MR image to the cine MR image to create an image transform; generating a corresponding cine ACF matrix using the image transform, and time-correlating the ACF matrix to a time-gated PET data set to produce an attenuation-corrected time-gated PET image. In embodiments, the baseline MR image is a composite image or an averaged image. The baseline MR image may be obtained while the structure is substantially static. The baseline MR image may also be obtained using a tissue differentiating scan protocol. In certain embodiments, the method also includes obtaining an additional cine MR image of the structure, wherein the cine MR image and the additional cine MR image use a same scan protocol. Registering the baseline MR image to the cine MR image may to create the image transform may include pixel intensity scaling or pixel intensity shifting. Registering the baseline MR image to the cine MR image to create the image transform may also include iteratively calculating mutual information of a joint pixel intensity histogram constructed from the baseline MR image and from an intermediate transform of the cine MR image. Registering the baseline MR image to the cine MR image to create the image transform can include establishing an image transform g that comprises rigid transformation parameters $\{\gamma, \theta, \phi, [t_x, t_y, t_z]\}$ and deformation coefficients $\{\delta_j\}$ for registering the baseline MR image to the cine MR image. Generating the corresponding cine ACF image matrix using the image transform, and time-correlating the ACF matrix to the time-gated PET data set to produce the attenuation-corrected time-gated PET image can include applying the cine ACF matrix to the time-gated PET data set. Moreover, generating the corresponding cine ACF image matrix using the image transform, and time-correlating the ACF matrix to the time-gated PET data set to produce the attenuation-corrected time-gated PET image may include applying to the time-gated PET data set one of a simple average, a time-weighted average, a velocity-weighted average, or a time-velocity-weighted average of plural cine ACF matrices that are time-correlated to the PET data set.

In yet other embodiments, an apparatus for producing an attenuation corrected time-gated PET image includes a PET-MR scanner, a controller connected in communication with the PET-MR scanner, wherein the controller is configured to obtain a baseline MR image, a cine MR image and a time-gated PET data set of a structure and an image processor connected in communication with the controller. The image processor is configured to register the baseline MR image to the cine MR image to create an image transform and to generate a corresponding cine ACF matrix using the image transform, and attenuation correct the time-gated PET data set based on the cine ACF matrix. The controller may be configured to time-correlate the cine ACF matrix to the time-gated PET data set. The image processor can be configured to time-correlate the cine ACF matrix to the time-gated PET data set. The image processor may also be configured to register the baseline MR image to the cine MR image using a locally perturbed rigid registration. In certain embodiments, the image processor is configured to register the baseline MR image to the cine MR image using a mutual information algorithm. The controller can be configured to obtain the baseline MR image while the structure is substantially static. The controller may also be configured to concurrently obtain the cine MR image and the PET data set while the structure is moving. In an embodiment, the image processor is configured to attenuation correct the time-gated PET data set using one of a simple average, a time-weighted average, a velocity-weighted average, or a time-velocity-weighted average of plural cine ACF matrices that are time-correlated to the PET data set.

In yet other embodiments, a method for attenuation correction of PET imaging in a respiratory-gated PET study includes obtaining a baseline MR image suitable for deriving PET attenuation correction factors, obtaining a cine MR image during a respiratory cycle, concurrent with the respiratory-gated PET study, and non-rigidly registering the baseline MR image to the cine MR image in order to produce a registered MR image that corresponds to a PET data set from the respiratory-gated PET study and is usable for deriving attenuation correction factors. The registered MR image is then used to form attenuation correction factors for the time-gated PET data set.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described embodiments, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for producing an attenuation-corrected time-gated PET image comprising:
    obtaining a baseline MR image and a cine MR image of a structure;
    registering the baseline MR image to the cine MR image to create an image transform; and
    generating a corresponding cine ACF matrix using the image transform, and time-correlating the ACF matrix to a time-gated PET data set to produce an attenuation-corrected time-gated PET image.

2. The method as claimed in claim 1, wherein the baseline MR image is a composite image.

3. The method as claimed in claim 1, wherein the baseline MR image is an averaged image.

4. The method as claimed in claim 1, wherein the baseline MR image is obtained while the structure is substantially static.

5. The method as claimed in claim 1, wherein the baseline MR image is obtained using a tissue differentiating scan protocol.

6. The method as claimed in claim 1, further comprising:
obtaining an additional cine MR image of the structure, wherein the cine MR image and the additional cine MR image use the same scan protocol.

7. The method as claimed in claim 1, wherein registering the baseline MR image to the cine MR image to create the image transform comprises pixel intensity scaling or pixel intensity shifting.

8. The method as claimed in claim 1, wherein registering the baseline MR image to the cine MR image to create the image transform comprises iteratively calculating mutual information of a joint pixel intensity histogram constructed from the baseline MR image and from an intermediate transform of the cine MR image.

9. The method as claimed in claim 1, wherein registering the baseline MR image to the cine MR image to create the image transform comprises:
establishing an image transform g that comprises rigid transformation parameters $\{\gamma, \theta, \phi, [t_x, t_y, t_z]\}$ and deformation coefficients $\{\delta_j\}$ for registering the baseline MR image to the cine MR image.

10. The method as claimed in claim 1, wherein generating the corresponding cine ACF image matrix using the image transform, and time-correlating the ACF matrix to the time-gated PET data set to produce the attenuation-corrected time-gated PET image:
comprises applying the cine ACF matrix to the time-gated PET data set.

11. The method as claimed in claim 10, wherein generating the corresponding cine ACF image matrix using the image transform, and time-correlating the ACF matrix to the time-gated PET data set to produce the attenuation-corrected time-gated PET image further comprises:
applying to the time-gated PET data set one of a simple average, a time-weighted average, a velocity-weighted average, or a time-velocity-weighted average of plural cine ACF matrices that are time-correlated to the PET data set.

12. An apparatus for producing an attenuation corrected time-gated PET image, said apparatus comprising:
a PET-MR scanner;
a controller connected in communication with the PET-MR scanner, wherein the controller is configured to obtain a baseline MR image, a cine MR image and a time-gated PET data set of a structure; and
an image processor connected in communication with the controller, wherein the image processor is configured to register the baseline MR image to the cine MR image to create an image transform; and
generate a corresponding cine ACF matrix using the image transform, and attenuation correct the time-gated PET data set based on the cine ACF matrix.

13. The apparatus as claimed in claim 12, wherein the controller is configured to time-correlate the cine ACF matrix to the time-gated PET data set.

14. The apparatus as claimed in claim 12, wherein the image processor is configured to time-correlate the cine ACF matrix to the time-gated PET data set.

15. The apparatus as claimed in claim 12, wherein the image processor is configured to register the baseline MR image to the cine MR image using a locally perturbed rigid registration.

16. The apparatus as claimed in claim 12, wherein the image processor is configured to register the baseline MR image to the cine MR image using a mutual information algorithm.

17. The apparatus as claimed in claim 12, wherein the controller is configured to obtain the baseline MR image while the structure is substantially static.

18. The apparatus as claimed in claim 12, wherein the controller is configured to concurrently obtain the cine MR image and the PET data set while the structure is moving.

19. The apparatus as claimed in claim 12, wherein the image processor is configured to attenuation correct the time-gated PET data set using one of a simple average, a time-weighted average, a velocity-weighted average, or a time-velocity-weighted average of plural cine ACF matrices that are time-correlated to the PET data set.

20. A method for attenuation correction of PET imaging in a respiratory-gated PET study, comprising:
obtaining a baseline MR image suitable for deriving PET attenuation correction factors;
obtaining a cine MR image during a respiratory cycle, concurrent with the respiratory-gated PET study; and
non-rigidly registering the baseline MR image to the cine MR image in order to produce a registered MR image that corresponds to a PET data set from the respiratory-gated PET study and is usable for deriving attenuation correction factors,
wherein the registered MR image then is used to form attenuation correction factors for the time-gated PET data set.

* * * * *